United States Patent
Hutchison et al.

[11] Patent Number: 5,340,079
[45] Date of Patent: Aug. 23, 1994

[54] HAND CONTROL VALVE

[76] Inventors: John W. Hutchison; Margaret B. Hutchison, both of 31 Columbia Ct., Walnut Creek, Calif. 94598

[21] Appl. No.: 144,340

[22] Filed: Nov. 1, 1993

[51] Int. Cl.[5] .................. F16K 25/00; F16K 31/60
[52] U.S. Cl. ............................ 251/85; 251/122; 251/243
[58] Field of Search ........... 251/122, 242, 243, 244, 251/245, 246, 85; 74/491, 519, 543, 545, 555

[56] References Cited

U.S. PATENT DOCUMENTS

| | | | |
|---|---|---|---|
| 504,235 | 8/1893 | Nicole | 251/245 |
| 538,317 | 4/1895 | Boynton | 251/243 |
| 612,947 | 10/1898 | Kiernan | 251/245 |
| 617,655 | 1/1899 | Ormerod | 251/245 |
| 1,016,956 | 2/1912 | Ramsey | 251/244 |
| 1,332,310 | 3/1920 | Shaver | 251/244 |
| 1,526,372 | 2/1925 | Pundzak | 251/245 |
| 2,035,202 | 3/1936 | Smith | 251/122 |
| 2,866,615 | 12/1958 | Hoesch | 251/245 |
| 4,677,774 | 7/1987 | Macchi | 251/245 |

Primary Examiner—George L. Walton
Attorney, Agent, or Firm—Myers & Associates, Ltd.

[57] ABSTRACT

A hand operated control valve for venting fluid pressure from a fluid line including a valve body having a vent port being controlled by a needle valve having an elongated shaft. The upper end of the elongated is affixed by a lift rod having a looped configuration to a pivotal lever. Upper and lower springs resiliently apply forces to the lever. Depression of the lever lifts the needle valve to progressively creates a variable flow opening for venting.

4 Claims, 1 Drawing Sheet

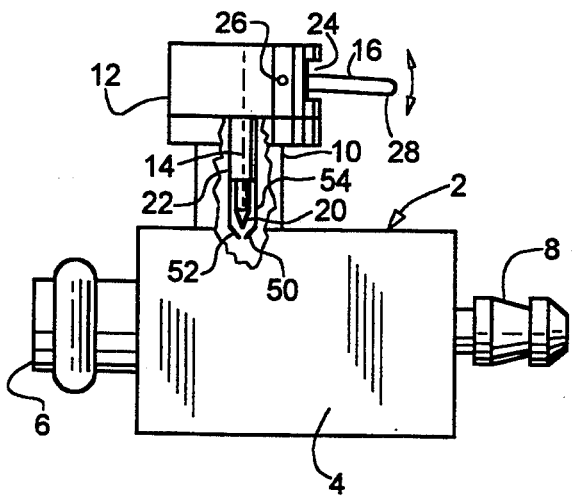
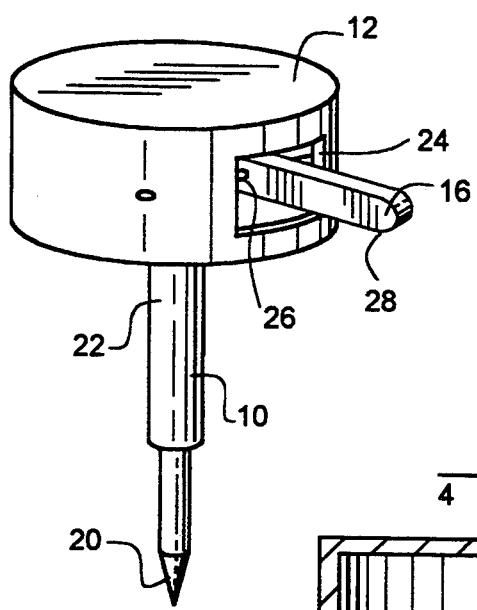
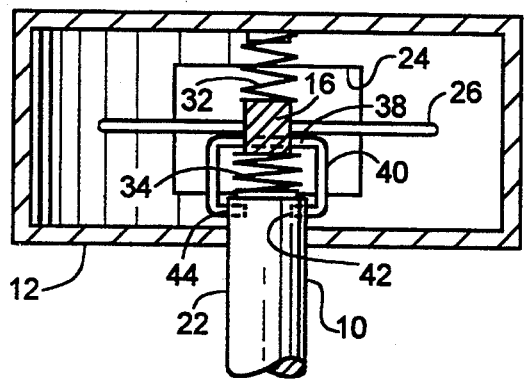
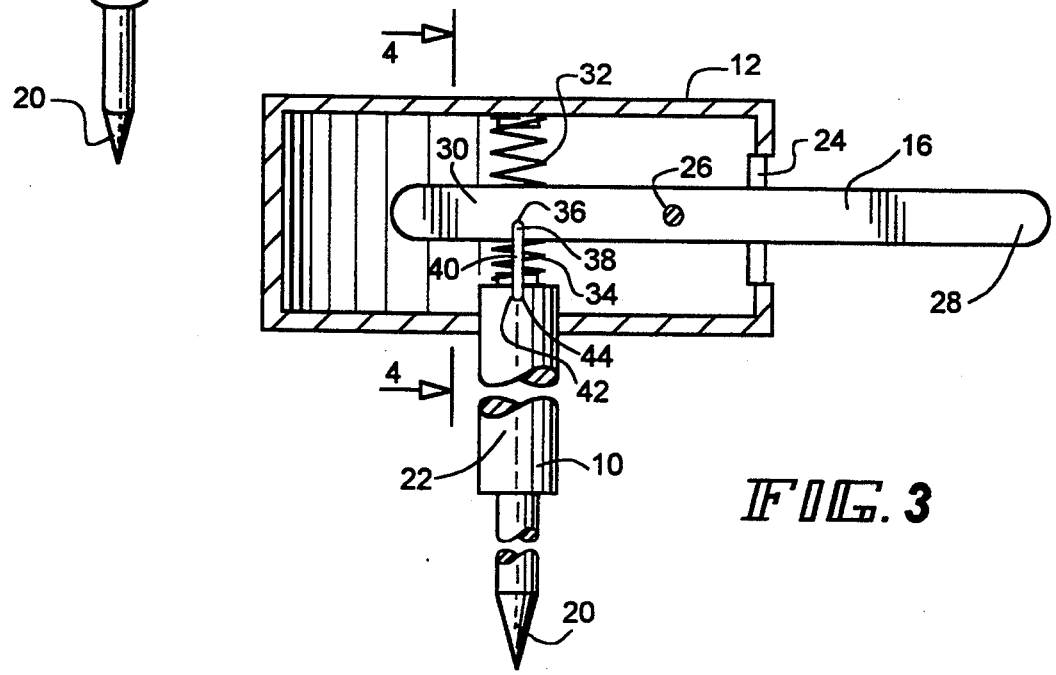

5,340,079

HAND CONTROL VALVE

BACKGROUND OF THE INVENTION

1. Field of the Invention

This invention relates in general to valves and more particularly, to a hand control valve for bleeding air and liquid.

2. Summary of the Prior Art

In many applications hand operated valves are used to bleed gas of liquid from a fluid line. An example of the use of such a hand operated valve is in a conventional apparatus for measuring blood pressure. The hand operated valves in blood pressure apparatus bleed air at a controlled rate during measurement. Prior valves in blood pressure devices commonly empty a screw top air valve which is difficult to operate and control bleeding. Moreover, screw type valves are relatively expensive to manufacture and are subject to wear of threads and other parts. In addition, a screw type valve does not provide the convenience of a controlled touch by the operator and is subject to alignment problems between the valve and seat. For these reasons, it is advantageous to provide an improved hand control valve for bleeding air and liquid from fluid lines.

SUMMARY OF THE INVENTION

It is therefore an objective of the invention to provide an improved hand operated valve for bleeding fluid lines. The valve of the invention is less bulky than previous lever type valves and can be used in many applications, including as the air bleed control in a blood pressure measuring apparatus. The valve herein disclosed includes a lever which can be operated with one hand with improved control of bleeding. The valve can be automatically reseated by simply releasing the spring biased lever. The lever of the valve of the invention requires a travel of less than 1/8th of an inch for either controlled bleeding or full dumping. The travel of the lever herein disclosed is controlled so that no undue pressure can be interfere with its function and is operated with either a soft or heavy touch by the operator. The design of the valve is simple in structure, inexpensive to manufacture, and is resistant to wear on the components during use.

BRIEF DESCRIPTION OF THE DRAWINGS

FIG. 1 is a side elevational view, with parts in section, of the hand operated control valve of the invention;

FIG. 2 is partial front perspective view of the needle valve stem and actuator cap of the control valve of FIG. 1;

FIG. 3 is a side elevational view, with parts in section, of the needle valve stem and actuator cap of the control valve of FIG. 1; and FIG. 4 is an end elevational view, with parts in section, of actuator cap shown in FIG. 3.

DESCRIPTION OF THE PREFERRED EMBODIMENT

Referring to FIG. 1 there is illustrated the hand operated control valve of the invention, generally designated by reference numeral 2. Control valve 2 is designed to bleed off a gas or liquid from a fluid line (not shown) at a control rate of flow as determined by the operator. Although not intended to be so limited, the control valve 2 can be used in a conventional blood pressure apparatus for measuring the blood pressure of an individual in which air is released from the device at a controlled rate during measurement. Control valve 2 includes a hollow valve body 4 having ports 6 and 8 for attachment to fluid line, such as in a blood pressure measuring device. A needle valve compartment 10 and hollow cap 12 are affixed to the top of body 4 and contain an elongated needle valve 14 and a needle valve actuator in the form of lever 16.

The needle valve 14 includes a conical needle valve tip 20 and an integral elongated shaft 22 extending to hollow cap 12. The hollow cap 12 is provided with a lever opening 24 through which the lever 16 extends. The lever 16 is pivotally affixed on lever pin 26 suitably mounted on the cap 12. The outer end portion 28 of lever 16 extends outward from cap 12 for manual operation by an operator. The opposite internal end portion 30 of lever 16 is operatively connected to elongated needle valve 14. Downward movement end portion 28 of the lever 16 for pivotal rotation about pivot pin 26 effects upper movement of the needle valve 14 in cooperation with upper spring 32 and lower spring 34. The internal end portion 30 of lever 16 (FIG. 3) includes a hole 36 for receiving the upper portion 38 of a lift rod 40 formed as continuous rectangular loop. The lower portion 42 of lift rod 40 extends through a hole 44 at the top of needle valve shaft 22. The lift rod 40 is designed to pivot in its mount holes and flex to allow a straight lift of the needle valve 14 without resistance or drag in the needle valve track.

The lower spring 34 is suitably affixed to the bottom of lever 16 and top needle valve shaft 22 around lift rod 40 to create a resilient force there between. The upper spring 32 is suitably attached to the top portion of lever 16 and cap 12 to provide a second resilient force. The resilient force of upper spring 32 and lower spring 34 are selected to bias the needle valve end 20 into closed relationship with valve orifice 50 in the neutral, non-depressed position of lever 16.

Valve orifice 50 is formed at the lower tip 52 of a hollow tube 54 which is in fluid communication with body 4 and extends upward in surrounding relationship to the needle valve 14. The orifice 50 is formed in the reduced end portion of tube 54 and is of a configuration to be closed by the conical needle valve tip 20 when inserted into orifice 50. Depression of the lever 16 causes the needle valve tip 20 to be lifted from the orifice 50 and creates a variable flow area dependent on the degree of movement of the valve tip 20 relative to orifice 50 up to a maximum flow or dump. Thus, the amount of depression of lever 16 and hence the degree of movement of needle valve 14 control the rate of flow through the valve and into the atmosphere. Maximum opening of orifice 50 can be attained with less than 1/8th of an inch of movement. Upon release of lever 16 by an operator, the conical needle valve tip 20 automatically moves down into seating relationship with orifice 50 for sealing. The design of the valve prevents the application of undue pressure on components, prevents misalignment of the needle valve, and eliminates excessive wear of its components.

What is claimed is:

1. A hand operated control valve comprising
a valve body being adapted to connected in fluid communication with a fluid conduit,
means forming an orifice for venting fluid pressure from valve body, a needle valve operatively connected to said means forming an orifice, said needle valve having a needle valve tip being movable from a closed seated position to an open position, said needle valve tip forming a variable flow opening between said closed and said open position for selectively controlling rate of venting of fluid pressure from said housing, an actuator operatively connected to said needle valve at an external position from said valve body, said actuator being manually operable to cause said movement, connection means coupling said lever to said elongated valve stem, said connection means having a first portion thereof above said actuator for causing said needle valve tip to be automatically seated in absence of any manual force being applied to said actuator, said connection means includes alignment means for maintaining alignment between said needle valve tip and said orifice during movement, said alignment means includes a lift rod connecting said actuator and said needle valve, said lift rod is pivotally connected to said actuator and said needle valve, and said lift rod is a closed loop having portions extending through a portion of said needle valve and said actuator and a second portion of said connection means being disposed between said closed loop and said valve stem for maintaining said alignment between said needle valve tip and said orifice during movement.

2. The control valve according to claim 1 wherein said actuator is a pivotally mounted lever.

3. The control valve according to claim 1 wherein said connection means includes resilient means first portion for biasing said valve tip into said seated position and for controlling the response of said actuator during manual manipulation.

4. The control valve according to claim 3 wherein said actuator is a lever pivotally mounted on a needle valve cap, said resilient means includes a pair of spring members respectively imposed between said level and said cap and between said lever and an upper portion of said needle valve.

* * * * *